United States Patent [19]

Nilsson et al.

[11] Patent Number: 5,728,559
[45] Date of Patent: Mar. 17, 1998

[54] SEPARATION OF PROTEINS

[75] Inventors: Birgitte Mahler Nilsson, Farum; Mads Aage Laustsen, Lyngby; Anders Rancke-Madsen, Charlottenlund, all of Denmark

[73] Assignee: Novo Nordisk A/S, Bagsvaerd, Denmark

[21] Appl. No.: 557,056

[22] PCT Filed: Jun. 23, 1994

[86] PCT No.: PCT/DK94/00256

§ 371 Date: Dec. 1, 1995

§ 102(e) Date: Dec. 1, 1995

[87] PCT Pub. No.: WO95/01989

PCT Pub. Date: Jan. 19, 1995

[30] Foreign Application Priority Data

Jul. 9, 1993 [DK] Denmark ................. 0830/93

[51] Int. Cl.$^6$ ................. C12N 9/00; C12N 9/20
[52] U.S. Cl. ................. 435/183; 435/219; 435/226; 435/232; 435/814
[58] Field of Search ................. 435/232, 816, 435/814, 815, 226, 219, 183

[56] References Cited

U.S. PATENT DOCUMENTS

| 4,340,676 | 7/1982 | Bourque | 435/232 |
|---|---|---|---|
| 4,400,471 | 8/1983 | Johal | 435/232 |
| 5,244,800 | 9/1993 | DeLucas et al. | 435/226 |

OTHER PUBLICATIONS

McPherson, A., Eur. J. Biochem., vol. 189, pp. 1–23 (1990).

*Primary Examiner*—Leon B. Lankford, Jr.
*Attorney, Agent, or Firm*—Steve T. Zelson, Esq.; Valeta Gregg, Esq.

[57] ABSTRACT

The present invention relates to a method of separating a protein, in particular an enzyme, from an aqueous solution of proteins, comprising (a) providing an aqueous mixture of proteins with a salt concentration at or below 1.5 Molar, to which a water soluble polymer has been added, and (b) recovery of the protein on crystalline form.

19 Claims, 8 Drawing Sheets

SEPARATION OF PROTEINS

TECHNICAL FIELD

The present invention relates to a method of separating a protein, in particular an enzyme, from an aqueous solution of proteins, and recovery of the desired protein on crystalline form.

BACKGROUND ART

Enzymes are usually provided as liquids or amorphous materials for industrial purposes. When not provided as liquids, they are usually provided as amorphous materials, because the known methods for crystallization of enzymes are usually regarded as too expensive to be used in an industrial scale. Due to the high purity of enzyme crystals, the provision of a cheap and simple method for crystallization of enzymes which is easily adaptable to an industrial scale is clearly a desideratum in the industry.

There is an abundance of literature concerning crystallization of enzymes. It is difficult to generalize in respect to the outcome of specific crystallization procedures. The art of enzyme crystallization is highly empirical, and a method shown to be successful for one group of enzymes does not have to be successful for other enzymes.

Characteristic features of the hitherto known protein crystallization processes are very pure and concentrated initial solutions, low yield, very long crystallization time, high consumption of chemicals including organic solvents, and poor industrial adaptability.

SUMMARY OF THE INVENTION

It is an object of the present invention to provide a process for the recovery of crystalline proteins, in particular enzymes, which process does not require the addition of large amounts of salts or organic solvents, which permits short crystallization times and high yields, and which is simple and cheap, and compatible to industrial requirements.

Accordingly, the present invention provides a method for separating a protein from an aqueous mixture of proteins comprising (a) providing an aqueous mixture of proteins with a salt concentration at or below 1.5 Molar, to which a water soluble polymer has been added (b) recovering the protein on crystalline form.

BRIEF DESCRIPTION OF DRAWINGS

The present invention is further illustrated by reference to the accompanying drawings, in which.

DETAILED DISCLOSURE OF THE INVENTION

Figure 1:
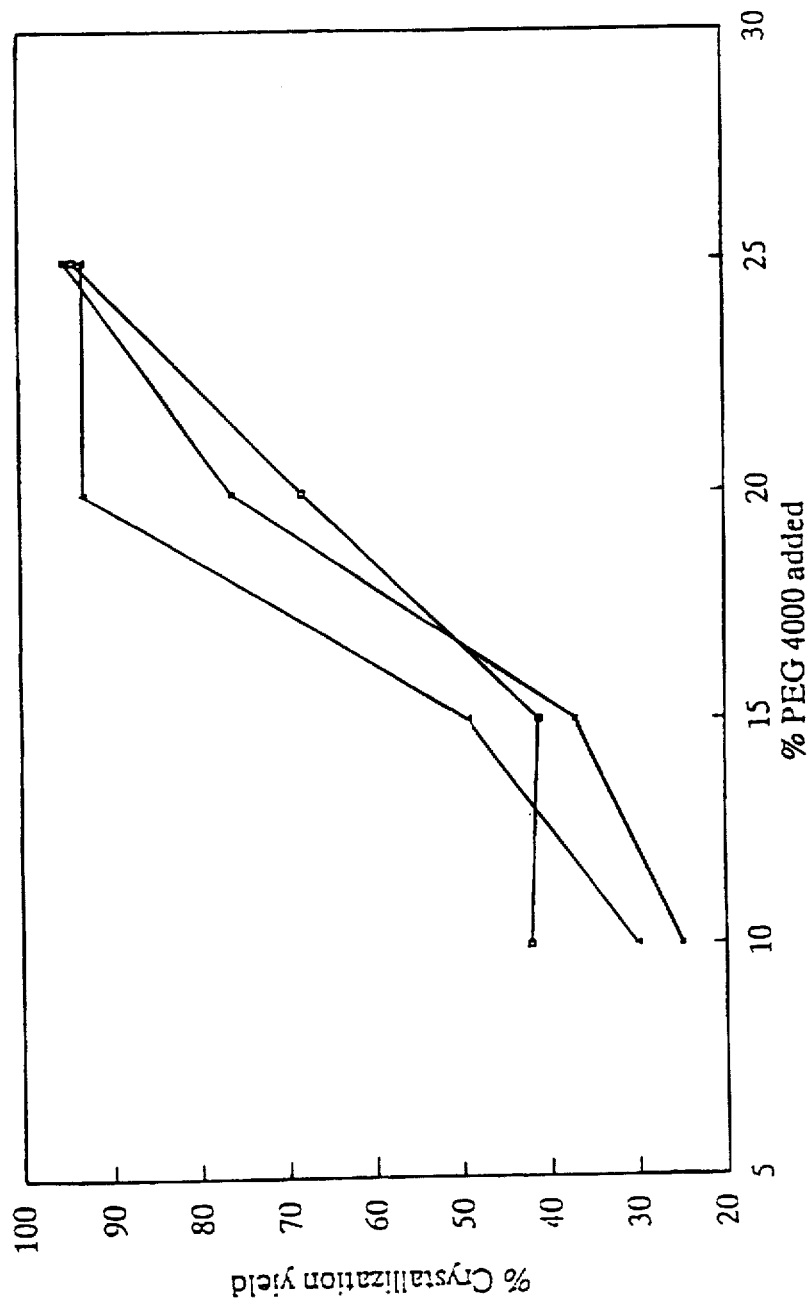
FIG. 1 shows the peroxidase crystallization yield (%) at various PEG 4000 concentrations and various $CaCl_2$ concentrations (■ 1% $CaCl_2$; ▲ 2% $CaCl_2$ and □ 2.5% $CaCl_2$).

The present invention provides a method for separating a protein or a polypeptide from an aqueous mixture comprising other proteins with different crystallization properties. It has surprisingly been found that by adding a water soluble polymer, e.g. polyethylene glycol, a protein may become separated from its mixture with other proteins and other impurities such as carbohydrate compounds, and precipitate on crystalline form.

Precipitation and crystallization of proteins with polyethylene glycol (PEG) is known from the literature together with the use of PEG to modify crystals for crystallography, however, the use of PEG crystallization for protein purification is new. The use of PEG has solely been for obtaining crystals for diffraction analysis, for reference see A. McPherson in Eur. J. Biochem. 189, 1990, pp.1–23; R. N. Haire et al. in Biopolymers Vol. 23 (12), 1984, pp. 2761–2779; and J. C. Lee et al. in J. Biol. Chem. 256(2), 1981, pp. 625–631.

It is generally accepted that part of the mechanism by which PEG acts is a salting out effect combined with a lowering of the dielectric properties of the solution, like for salt and organic solvent induced crystallizations. Besides that, PEG under certain conditions seems to be able to exclude protein from the solution by increasing the thermodynamic activity of the protein resulting in an amorphous PEG poor phase from which the amorphous protein precipitate potentially can convert into protein crystals, cf. R. N. Haire et al. in Biopolymers Vol. 23(12), 1984, pp. 2761–2779.

Another use of PEG for protein crystallization has been the creation of an aqueous 2-phase system by the use of PEG and high salt concentrations, in which the protein is concentrated in the PEG phase, nucleation takes place in the interphase and the crystal growth is occurring in the water phase with the driving force being the high salt concentration, for reference see Eur. J. Biochem. 189, 1990, pp. 1–23.

From studies according to the invention a different and surprising mechanism seems to be the explanation for the crystallizations, with the fundamental difference being that the crystallization is driven by an affinity between the PEG molecules and the protein at a relatively low salt concentration. The result of that is a phase separation where the protein is concentrated in a soluble form into micro droplets in which nucleation and crystal growth take place as described below:

When PEG is added to the protein solution (in concentrations which do not create a 2 phase system by itself), protein with affinity to PEG will associate with the PEG molecules creating an inhomogeneous solution, which at the right PEG MW, PEG concentration, salt concentration and protein concentration can grow into a system consisting of a water phase with a lowered protein concentration and micro droplets with a very high protein concentration. This system seems to be quite different from a normal aqueous 2-phase system, as the phases cannot be separated by traditional low speed centrifugation; however, at ultracentrifugation (for instance as described in Example 11), it is possible to see two phases.

In the droplets with high protein concentration and probably with some exclusion of impurities, optimum conditions for crystal formation appear. The crystals then apparently take form in the droplets until they reach a size where they might burst out of the droplets generating a normal one phase aqueous system with solid crystals at the end of the crystallization. However, dependent on the protein in question, the system can as well end up as a 2-phase system with the bulk part of the crystals still in the droplet phase. Examples of crystal growth occurring both in the droplet phase and from the surface of the droplets out in the surrounding solution have also been observed.

This proposed mechanism where the protein is crystallized in a 2-phase droplet system with the protein in a purified and concentrated form created by the affinity between a water soluble polymer and the protein suggests that the technique can be very powerful even for low concentrated and impure protein solutions.

The method of the invention can be applied to separation of a protein from a mixture of proteins, in particular to separation of an enzyme from a mixture of proteins. In a preferred embodiment, the enzyme containing solution is a culture broth obtained by cultivation of an enzyme producing microorganism. Preferably the method of the invention is applied to a culture broth that has first been subjected to solid/liquid separatory techniques, e.g. by flocculation, centrifugation, filtration or micro filtration. It may also be useful to purify by precipitation or use of chromatographic methods before crystallization.

In a more specific embodiment, the method of invention comprises concentration of the enzyme containing solution by methods known per se. Such methods include concentration by ultrafiltration, by diafiltration, by dialysation, or by evaporation.

Concentration of the protein containing solution, although not essential for carrying out crystallization, is convenient from a handling and a yield perspective. For practical reasons the enzyme containing solution may be concentrated to a content of enzyme protein of from 0.1 to 25% w/w, more preferred of from 0.5 to 15% w/w, most preferred of from 1 to 10% w/w.

In a preferred embodiment, the method is applied to separation of oxidoreductases, proteases, lipases, amylases and cellulases. Oxidoreductases, which are defined and described in "Enzyme Nomenclature 1992, Academic press, Inc., San Diego", belong to a class of enzymes that catalyses transfer of electrons from one substance to another (oxidation-reduction). Oxidoreductases include dehydrogenases, reductases, oxidases, transhydrogenases, catalases, peroxidases, and oxygenases.

More specific examples include horseradish peroxidase, ligninases and other peroxidases, and oxidases such as laccases. These enzymes are preferably of microbial origin.

Examples of microorganism genera which may be used for production of suitable oxidoreductases are: Trametes, Rhizoctonia, Pseudomonas, Bacillus, Streptomyces, Hygrophorus, Coprinus, Polyporus, Candida, Curvularia, Cercospora, Mycoliophtora, Aspergillus, and Scytalidium. The invention, however, is not restricted to enzymes derived from the above mentioned taxa. All microorganisms producing oxidoreductases with the desired properties may be used in relation to this invention.

The oxidoreductase is preferably a laccase (EC 1.10.3.2), a catalase (EC 1.11.1.6), a peroxidase (EC 1.11.1.7), or an oxidase.

In a preferred embodiment, the method of invention is applied to a peroxidase containing solution and to a catalase containing solution.

A suitable peroxidase is one producible by plants (e.g. horseradish peroxidase) or microorganisms such as fungi or bacteria. In a preferred embodiment, the peroxidase is derived from Coprinus, e.g. *C. cinereus* or *C. macrorhizus*, or from Bacillus, e.g. *B. pumilus*, particularly a peroxidase according to International Patent Application WO 91/05858.

The enzyme may furthermore be one which is producible by a method comprising cultivating a host cell transformed with a recombinant DNA vector which carries a DNA sequence encoding said enzyme as well as DNA sequences encoding functions permitting the expression of the DNA sequence encoding the enzyme in a culture medium under conditions permitting the expression of the enzyme and recovering the enzyme from the culture.

Particularly, a recombinantly produced peroxidase is a peroxidase derived from a Coprinus sp., in particular *C. macrorhizus* or *C. cinereus* according to WO 92/16634.

Catalases are known both from animal sources (e.g. cow liver) and from many different microorganisms. JP Patent Application 2-76579 discloses catalase from *Aspergillus niger* strain NFAG-2. GB Patent No. 2,216,149 discloses catalase from Penicillium. In a preferred embodiment of the invention the catalase is obtained from strains of Scytalidium and Humicola as described in WO 92/17571.

In another preferred embodiment of the method according to the invention the enzyme is a protease. Suitable proteases include those of animal, vegetable or microbial origin. Microbial origin is preferred. Chemically or genetically modified mutants are included. It may be a serine protease, preferably an alkaline microbial protease or a trypsin-like protease. Examples of alkaline proteases are subtilisins, especially those derived from Bacillus, e.g. subtilisin Novo, subtilisin Carlsberg, subtilisin 309, subtilisin 147 and subtilisin 168 (described in WO 89/06279). Examples of commercial Bacillus subtilisins are Alcalase®, Savinase®, Esperase® and Durazym™ products of Novo Nordisk A/S. Examples of trypsin-like proteases are trypsin (e.g. of porcine or bovine origin) and the Fusarium protease described in WO 89/06270.

In another preferred embodiment of the method according to the invention the enzyme is a lipase. Suitable lipases include those of bacterial and fungal origin. Chemically or genetically modified mutants are included. Particularly preferred is lipase obtainable from Pseudomonas, Candida and Mucor, in particular *Pseudomonas cepaciae*, as described in EP 0 214 761, or lipase obtained by cloning the gene from *Humicola lanuginosa* and expressing the gene in *Aspergillus oryzae* as described in EP 0 258 068, available under the trade mark Lipolase® from Novo Nordisk A/S.

In another preferred embodiment of the method according to the invention the enzyme is an amylase. Suitable amylases include those of bacterial and fungal origin. Chemically or genetically modified mutants are included. Amylases include, for example, α-amylases obtained from Bacillus, e.g. *B. licheniformis*, described in more detail in British Patent Specification No. 1,296,839.

In another preferred embodiment of the method according to the invention the enzyme is a cellulase. Suitable cellulases include those of bacterial and fungal origin, in particular cellulases from fungi are preferred. Chemically or genetically modified mutants are included. Examples of fungi which may be used for production of suitable cellulases are: Trichoderma, Phanerochaete, Humicola, Fusarium and Myceliopthora.

The method of invention further comprises addition of a water soluble polymer.

Preferred water soluble polymers are glycols and amines, e.g. polyamines. More preferred are polyethylene glycol and polypropylene glycol. Most preferred are polyethylene glycols with a MW of from 200 to 10000.

Water soluble polymers may be added in concentrations of 1–50% w/w, preferably 2–40% w/w.

According to the invention the method may additionally comprise adding a salt in a concentration of up to 1.5 Molar, preferably in a concentration of up to 1.0 Molar.

Preferred salts are salts of Magnesium, Calcium, Sodium, Potassium and Ammonium. Most preferred are salts in which the anion is selected from the group consisting of Chloride, Formiate, Acetate and Sulphate.

By the method of the invention the pH of the concentrated aqueous solution, to which a water soluble polymer has been added, may be adjusted to the optimum of the crystallization; in some cases optimum of the crystallization is at a level around pI of the enzyme. In a preferred embodiment, pH is adjusted to a level of pH=pI±1.

For adjustment of pH virtually any acid or base can be used. The acid may be inorganic or organic. Some examples are hydrochloric acid, sulfuric acid, nitrous acid, phosphoric acid, acetic acid, citric acid, and formic acid. Preferred acids are formic acid, citric acid, and acetic acid. A preferred base is sodium hydroxide.

In a particular embodiment of the invention salt is added to the aqueous mixture of proteins in a concentration of up to 1.5 Molar, preferably in a concentration of up to 1.0 Molar, and the pH of the solution is adjusted to the optimum of the crystallization.

The method of invention causes the protein, in particular the enzyme, to precipitate on crystalline form. Recovery of the crystalline protein may be accomplished by conventional methods, e.g. by filtration and subsequent drying, or by redissolution of the crystals for the manufacture of liquid protein products.

The following examples further illustrate the present invention, and they are not intended to be in any way limiting to the scope of the invention as claimed.

EXAMPLE 1

Effect of Water Soluble Polymer

A culture broth containing *Coprinus cinereus* peroxidase, obtained as described in EP Patent Application No. 505,311, was subjected to the method of invention.

Initially, the culture broth was subjected to solid/liquid separation by centrifugation. An ultrafiltrate containing 5.5% w/w DS (dry substance) peroxidase protein and 2.4% w/w DS other enzymes was obtained.

Polyethylene glycol (PEG 4000) and $CaCl_2 \cdot 2H_2O$ were added in various amounts (cf. FIG. 1), and pH was adjusted to pH 4.0 by addition of formic acid. The solution was stirred at 28° C. for 24 hours.

The crystallization yields at various PEG and salt concentrations (■ 1% $CaCl_2$; ▲ 2% $CaCl_2$ and □ 2.5% $CaCl_2$) are shown in the appended FIG. 1.

EXAMPLE 2

Effect of pH

A culture broth containing *Coprinus cinereus* peroxidase, obtained as described in EP Patent Application No. 505,311, was subjected to the method of invention.

Initially, the culture broth was subjected to solid/liquid separation by centrifugation. An ultrafiltrate containing 5.5% w/w DS (dry substance) peroxidase protein and 2.4% w/w DS other enzymes was obtained.

To this solution 20% w/w of polyethylene glycol (PEG 4000) and 1.5% w/w of $CaCl_2 \cdot 2H_2O$ were added, and pH was adjusted to various pH values with formic acid. The solution was stirred at 28° C. for 24 hours.

Figure 2:
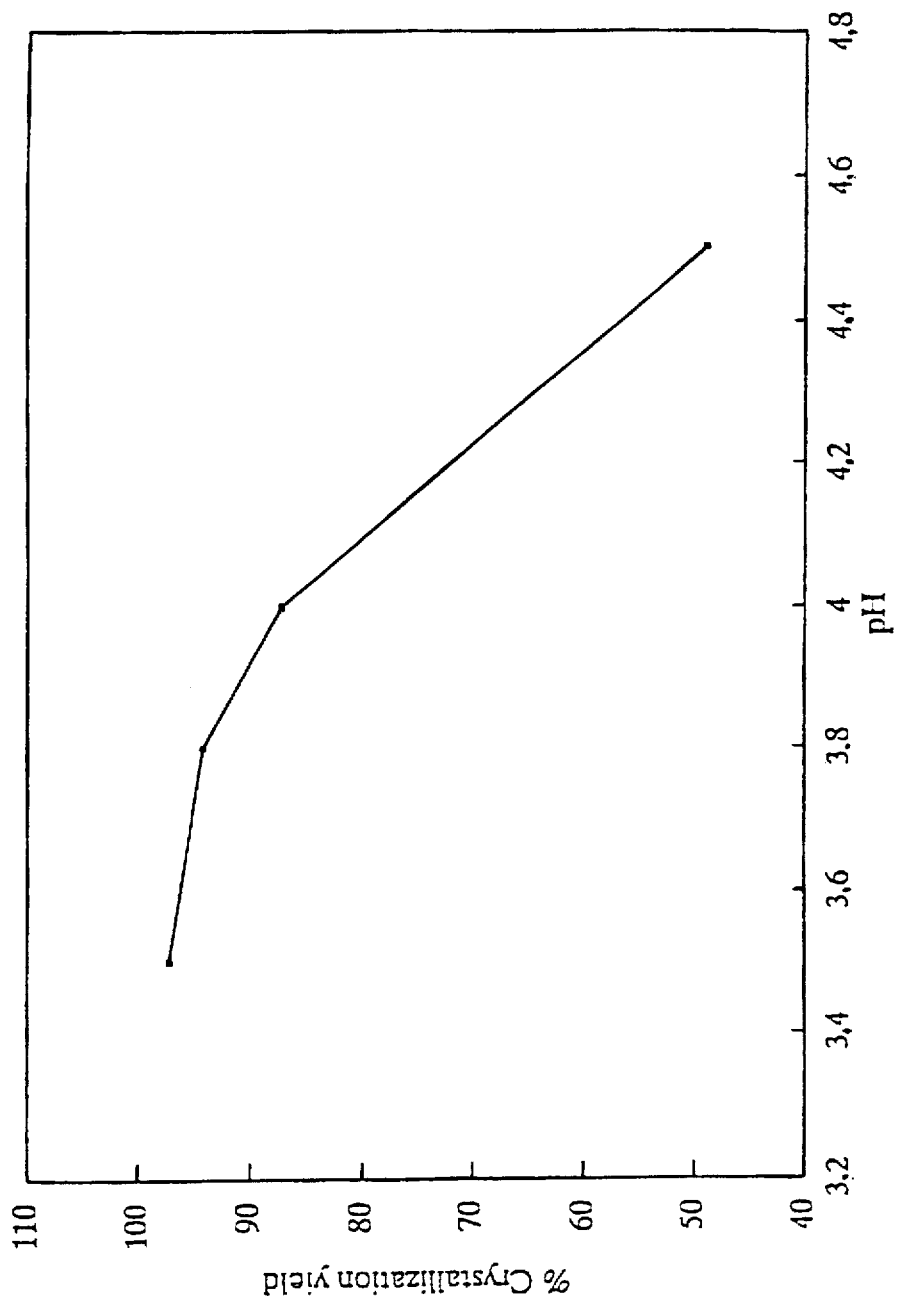
FIG. 2 shows the peroxidase crystallization yield (%) at various pH values.

The crystallization yields at various pH are shown in the appended FIG. 2.

EXAMPLE 3

Effect of Concentrations

A culture broth containing *Coprinus cinereus* peroxidase, obtained as described in EP Patent Application No. 505,311, was subjected to the method of invention.

Initially, the culture broth was subjected to solid/liquid separation by centrifugation. Subsequently several ultrafiltrates containing various concentrations of peroxidase protein and other enzymes were obtained.

To each of these solutions 1.5% w/w of $CaCl_2 \cdot 2H_2O$ were added. Polyethylene glycol (PEG 4000) was added in various amounts. pH was adjusted to pH 4.0 with formic acid, and the solutions were stirred at 28° C. for 24 hours.

Figure 3:
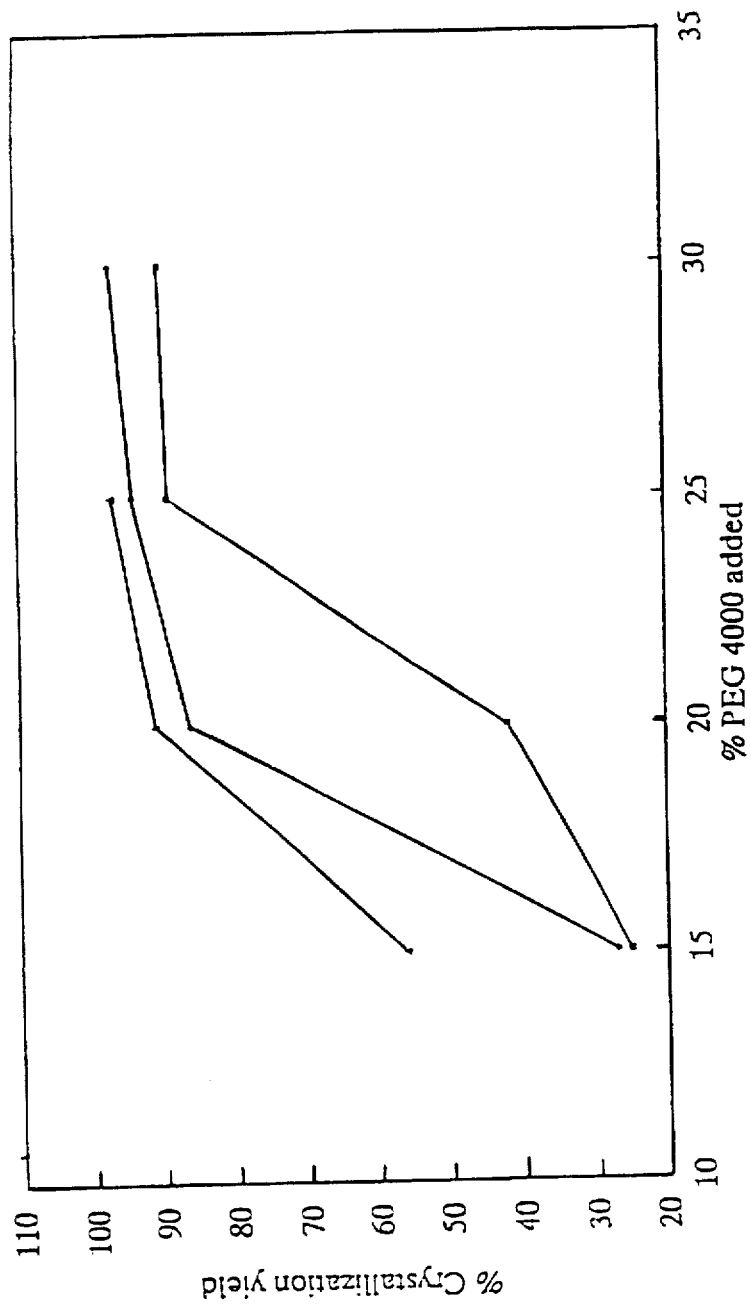
FIG. 3 shows the peroxidase crystallization yield (%) at various enzyme and PEG 4000 concentrations (■ 3% peroxidase and 1.4% other enzymes; ♦ 4.8% peroxidase and 2.3% other enzymes and ▲ 6.7% peroxidase and 3.1% other enzymes).

The crystallization yields at various enzyme and PEG concentrations (■ 3% peroxidase and 1.4% other enzymes; ♦ 4.8% peroxidase and 2.3% other enzymes and ▲ 6.7% peroxidase and 3.1% other enzymes) are shown in the appended FIG. 3.

EXAMPLE 4

Crystallization of Catalase

A culture broth containing *Scytalidium thermofilum* catalase, obtained as described in WO 92/17571, was subjected to the method of invention.

Initially, the culture broth was subjected to solid/liquid separation by flocculation and filtration. Subsequently the filtrate was concentrated by evaporation and ultra-/diafiltration. The concentrate contained 1.2% w/w DS (dry substance) catalase protein and 5.5% w/w total dry substance.

Polyethylene glycol (PEG 4000) and $CaCl_2 \cdot 2H_2O$ were added in various amounts (cf. FIG. 4), and pH was adjusted to pH 6.8. The solution was stirred at 28° C. for 48 hours.

Figure 4:
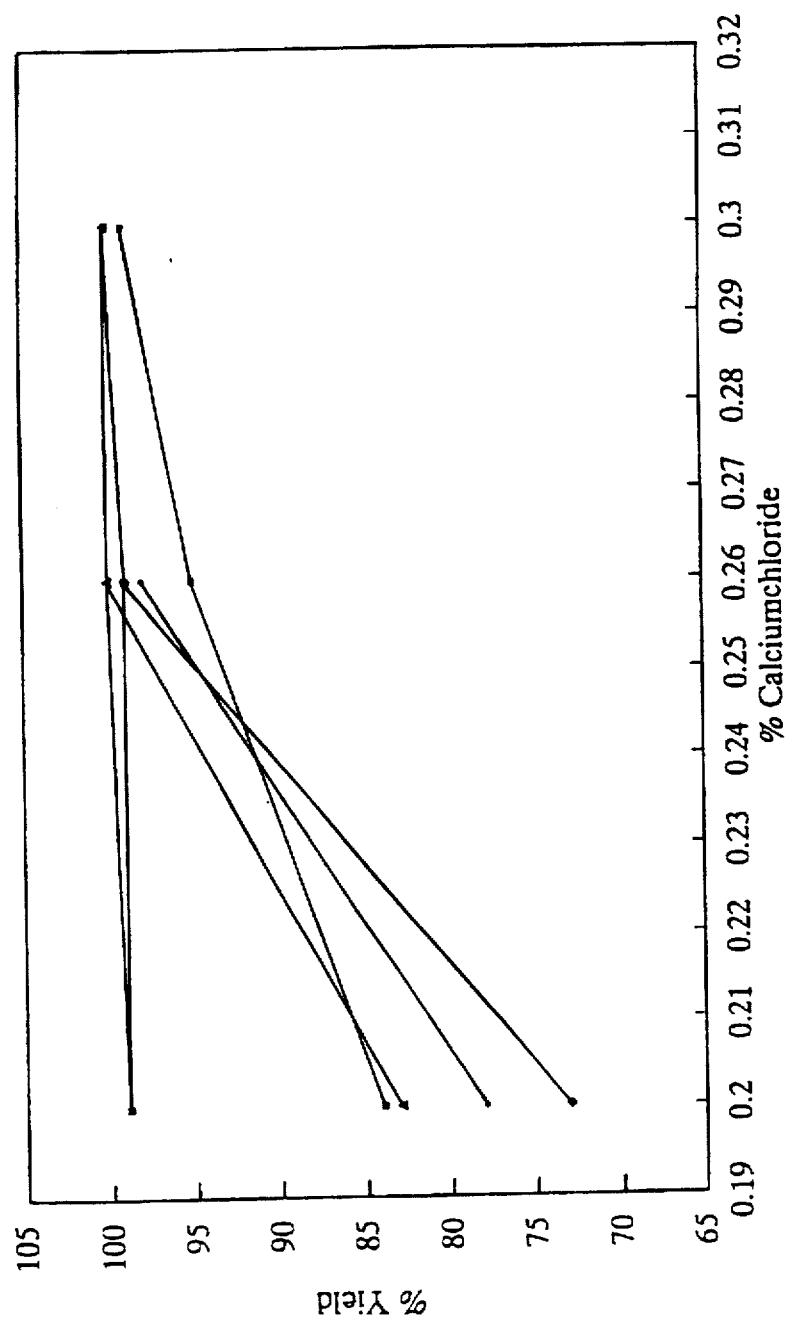
FIG. 4 shows the catalase crystallization yield (%) at various $CaCl_2$-concentrations and at various PEG 4000 concentrations (■ 20% PEG 4000; ♦ 22% PEG 4000; ▲ 24% PEG 4000; ▲ 26% PEG 4000; ◊ 28% PEG 4000 and ∆ 30% PEG 4000).

The crystallization yields at various $CaCl_2$-concentrations and at various PEG 4000-concentrations (■ 20% PEG 4000; ♦ 22% PEG 4000; ▲ 24% PEG 4000; □ 26% PEG 4000; ◇ 28% PEG 4000 and Δ 30% PEG 4000) are shown in the appended FIG. 4.

EXAMPLE 5

Crystallization of Catalase

A culture broth containing *Scytalidium thermofilum* catalase, obtained as described in WO 92/17571, was subjected to the method of invention.

Initially, the culture broth was subjected to solid/liquid separation by flocculation and filtration. Subsequently the filtrate was concentrated by evaporation. The concentrate contained 0.28% w/w DS (dry substance) catalase protein and 9.2% w/w total dry substance.

Polyethylene glycol (PEG 4000) and $CaCl_2 \cdot 2H_2O$ were added in various amounts (cf. FIG. 5), and pH was adjusted to pH 6.0–6.5. The solution was stirred at 28° C. for 48 hours.

Figure 5:
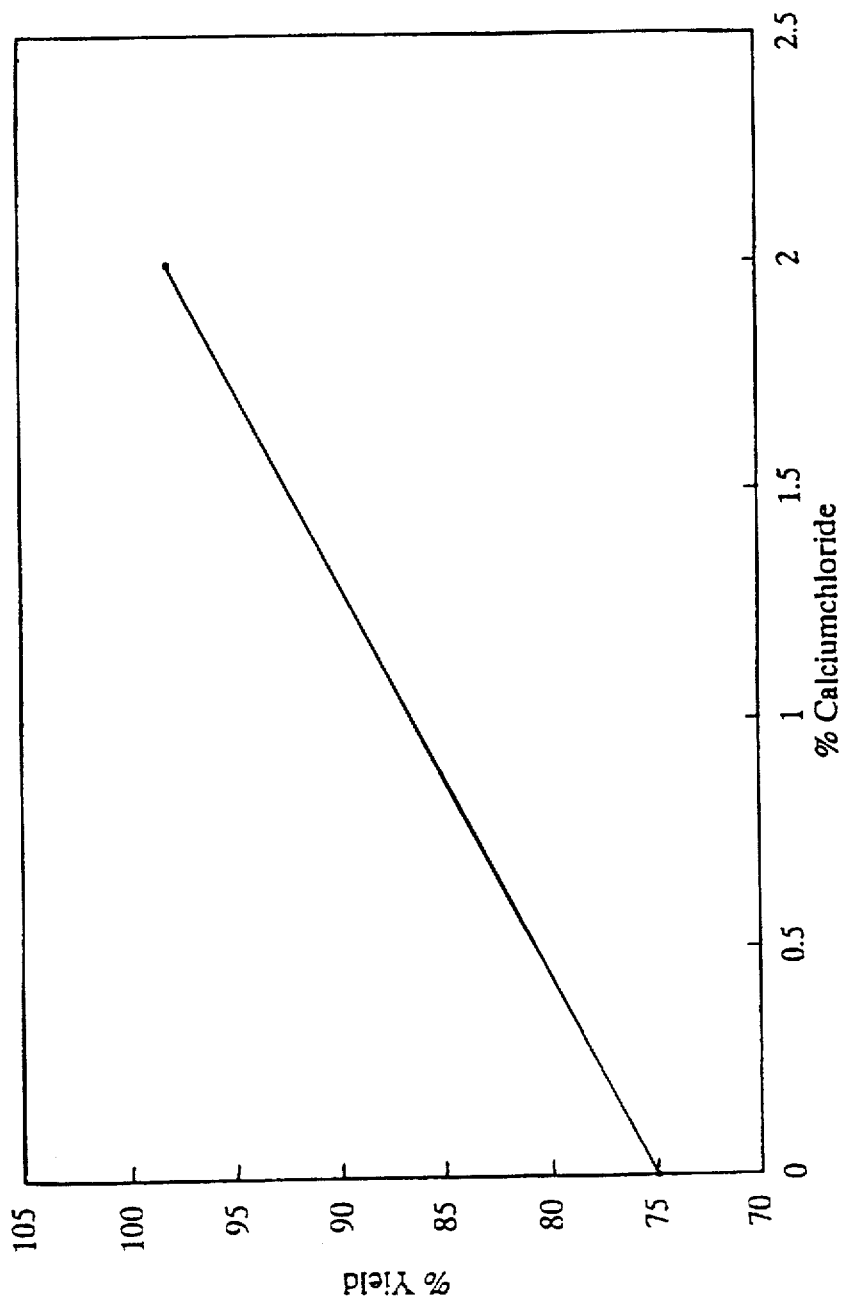
FIG. 5 shows the catalase crystallization yield (%) at various $CaCl_2$-concentrations and at various PEG 4000 concentrations (■ 20% PEG 4000 and ♦ 25% PEG 4000).

The crystallization yields at various $CaCl_2$-concentrations and at various PEG 4000-concentrations (■ 20% PEG 4000 and ♦ 25% PEG 4000) are shown in the appended FIG. 5.

EXAMPLE 6

Crystallization of Catalase

A culture broth containing *Scytalidium thermofilum* catalase, obtained as described in WO 92/17571, was subjected to the method of invention.

Initially, the culture broth was subjected to solid/liquid separation by flocculation and filtration. Subsequently the filtrate was concentrated by evaporation. The concentrate contained 0.28% w/w DS (dry substance) catalase protein and 9.2% w/w total dry substance.

Polyethylene glycol (PEG 1500 and $CaCl_2;2H_2O$ were added in various amounts (cf. FIG. 6), and pH was adjusted to pH 6.5–7.0. The solution was stirred at 28° C. for 48 hours.

Figure 6:
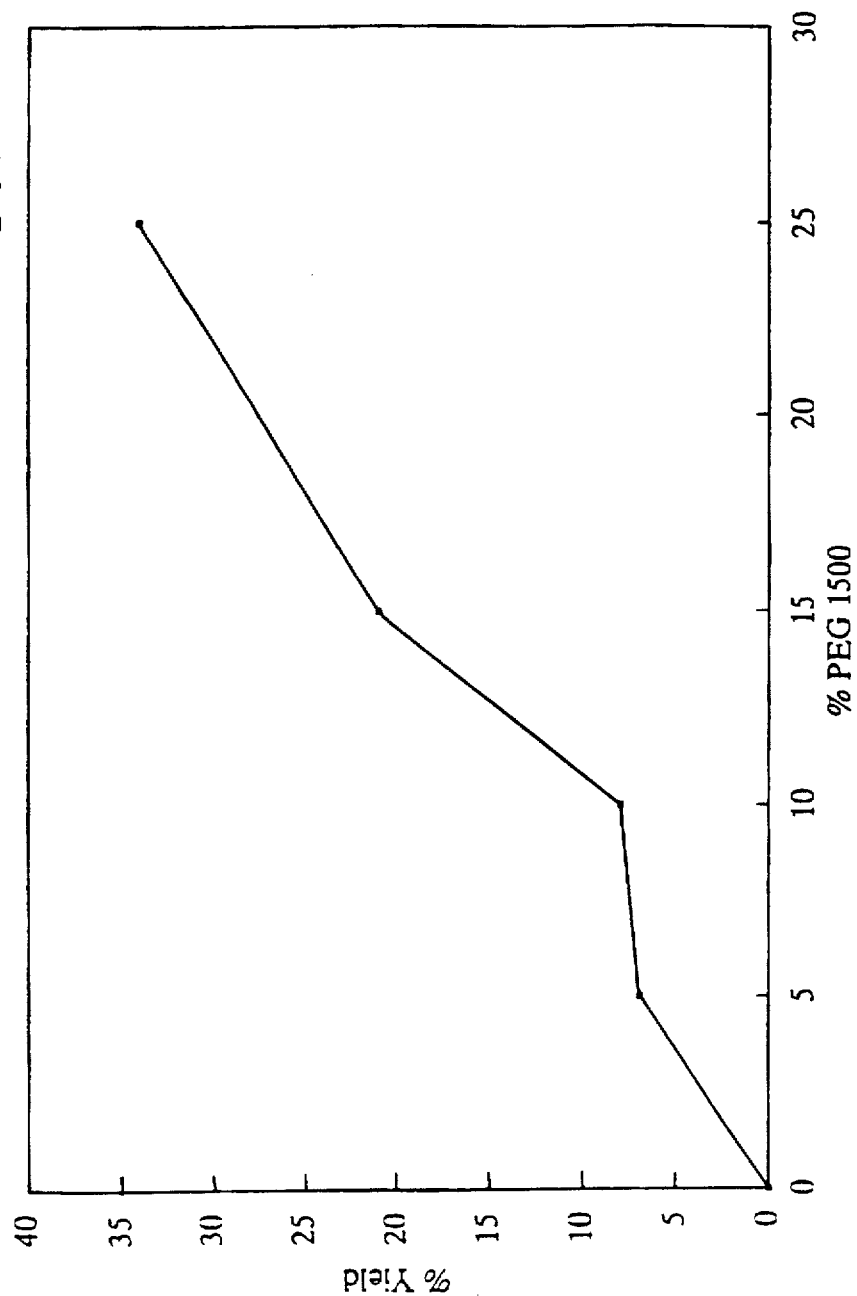
FIG. 6 shows the catalase crystallization yield at various PEG 1500 concentrations and a $CaCl_2$-concentration of 0.2%.

The crystallization yields at various PEG 1500 concentrations and a $CaCl_2$-concentration of 0.2% are shown in the appended FIG. 6.

EXAMPLE 7

Crystallization of Protease

A culture broth containing protease (Savinase®) from *Bacillus lentus*, (U.S. Pat. No. 3,723,250), was subjected to the method of invention.

Initially, the culture broth was subjected to solid/liquid separation by flocculation and centrifugation. Subsequently the supernatant was concentrated by ultrafiltration. The concentrate contained 9.2% w/w DS (dry substance) protease protein and 19.6% w/w total dry substance. The conductivity was 1.55 mS/cm.

Polyethylene glycol (PEG 4000) was added in various amounts (cf. FIG. 7), and pH was adjusted to pH to 5.6. The solution was stirred at 28° C. for 24 hours.

Figure 7:
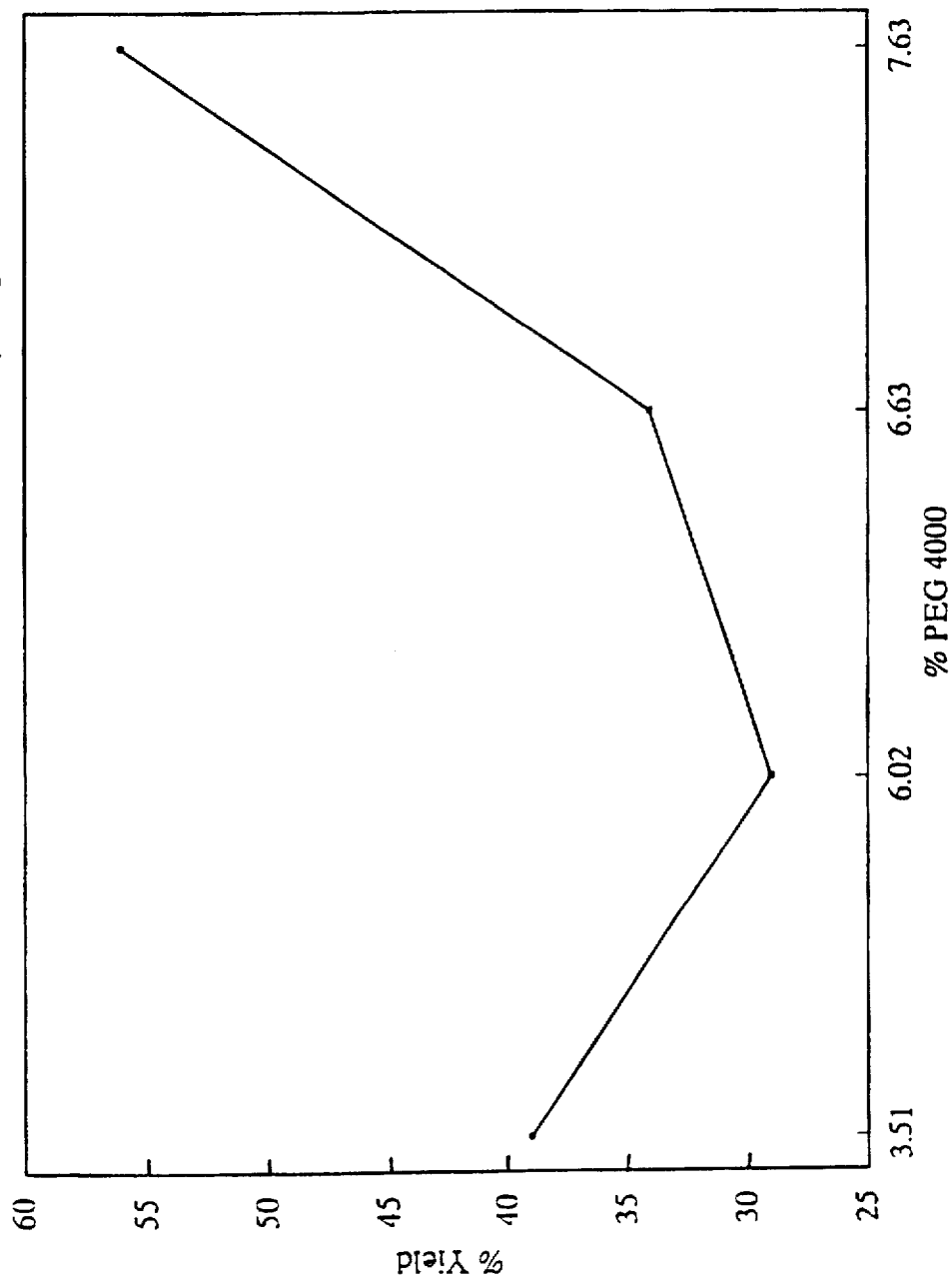
FIG. 7 shows the protease crystallization yield (%) at various PEG 4000-concentrations.

The crystallization yields at the various PEG concentrations are shown in the appended FIG. 7.

EXAMPLE 8

Crystallization of Protease

A culture broth containing protease (Savinase®) from *Bacillus lentus*, (U.S. Pat. No. 3,723,250), was subjected to the method of invention.

Initially, the culture broth was subjected to solid/liquid separation by flocculation and centrifugation. Subsequently the supernatant was concentrated by ultrafiltration. The concentrate contained 9.2% w/w DS (dry substance) protease protein and 19.6% w/w total dry substance. The conductivity was 1.55 mS/cm.

Polyethylene glycol (PEG 4000) was added in various amounts together with 1.1% w/w $CaCl_2;2H_2O$, and pH was adjusted to pH 5.6. The solution was stirred at 28° C. for 24 hours.

Figure 8:
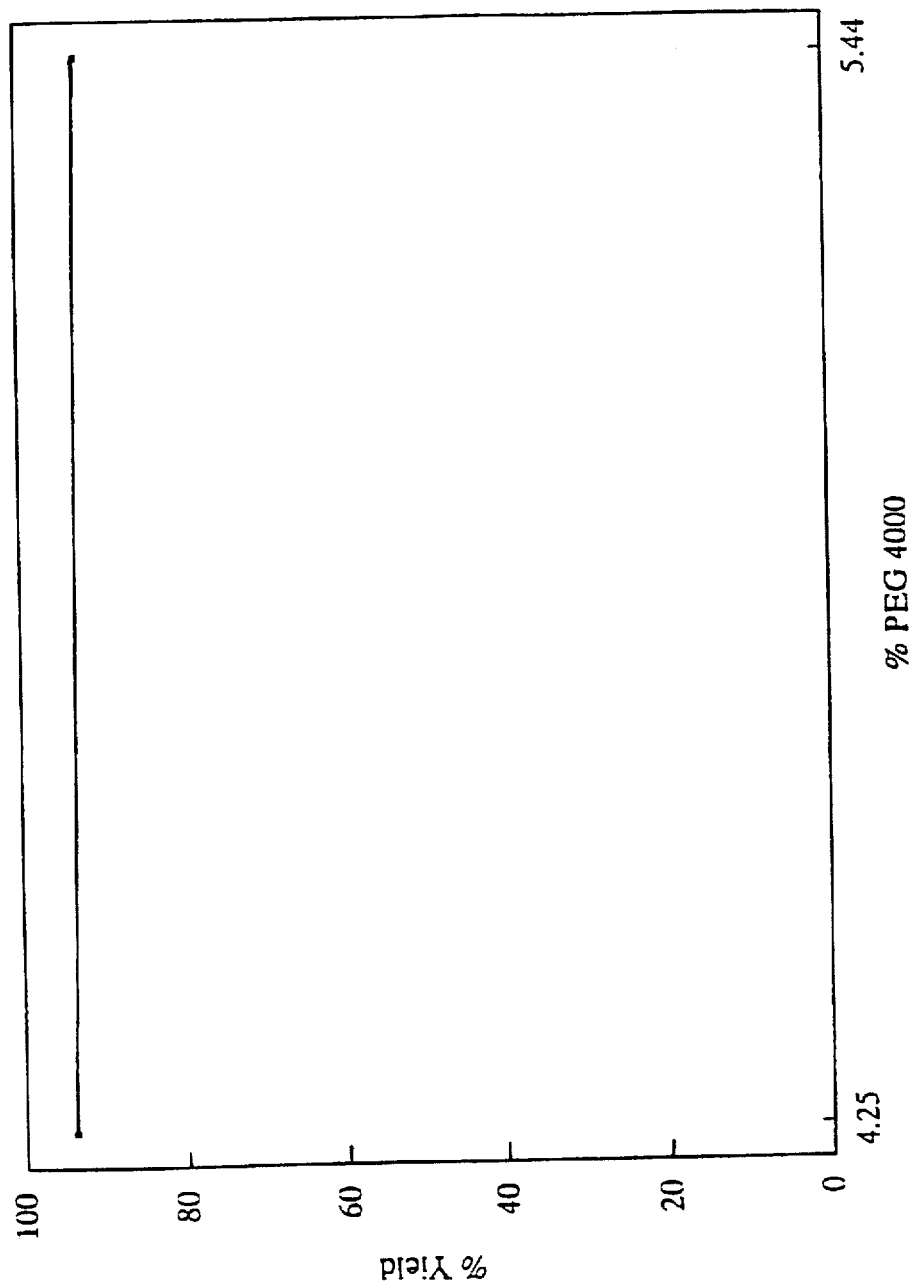
FIG. 8 shows the protease crystallization yield (%) at various PEG 4000-concentrations and with a $CaCl_2$-concentration of 1.1%.

The crystallization yields at the various PEG concentrations are shown in the appended FIG. 8.

EXAMPLE 9

Crystallization of Lipase

A concentrate containing Lipase from *Pseudomonas cepaciae*, obtained as described in EP 0 214 761, was subjected to the method of the invention.

To the concentrate containing 2.1% w/w DS Lipase protein and 20% w/w total DS, 31% PEG 4000 was added at pH 7.8. The solution was stirred at 28° C. for 24 hours.

The crystallization yield was then 47%.

EXAMPLE 10

Crystallization of Cellulase

*Humicola insolens* Cellulase, obtained as described in WO 91/17244, was produced by fermentation and recovered by filtration, ultrafiltration and diafiltration with ionexchanged water.

The concentrated cellulase solution had an enzyme concentration of 105 g/l, an enzyme purity of 58% of the dry matter content and a protein purity of 88%. pH was 7.0 and the conductivity was 607 µS.

39.6 g of PEG 300 per 100 g of cellulase solution were added under stirring. The temperature was 27° C. After 20 hours the crystals were harvested by centrifugation and redissolved in 0.5% NaCl solution. The crystal yield was 83% determined on enzyme activity with a cellulase protein purity of 100%.

EXAMPLE 11

Characterization of the PEG/Enzyme System

When PEG and salt are added to an enzyme concentrate, enzyme rich micro droplets are formed and crystallization takes place within these droplets. The two phases can be separated by ultracentrifugation.

A culture broth containing *Coprinus cinereus* peroxidase, obtained as described in EP 505 311, was subjected to the method of the invention.

Initially, the culture broth was subjected to solid/liquid separation by centrifugation. An ultrafiltrate containing 5.1% w/w DS (dry substance) peroxidase protein was obtained. 20% PEG 4000 and 1.5% w/w $CaCl_2;2H_2O$ were added to the concentrate and pH was adjusted to pH 4.0. Immediately after mixing micro droplets were observed in the liquid by use of a microscope. By ultracentrifugation (27000 g in 15 min.) two phases could be separated. The peroxidase content is measured as $A_{405}$ and compared to the total protein content measured as $A_{280}$. The results are presented in Table 1. It can be seen that the peroxidase is concentrated and purified within these micro droplets.

TABLE 1

|  | $A_{405}$ | $A_{405}/A_{280}$ | KPOXU*/g |
|---|---|---|---|
| Bottom-phase: | 388 | 1.35 | 472 |
| Top-phase: | 31 | 0.82 | 33 |
| Concentrate, before addition of PEG and salt: | 169 | 1.16 | 172 |
| Redissolved crystals |  | 2.0 |  |

*Determination of peroxidase activity (POXU): 1 peroxidase unit (POXU) is the amount of enzyme that catalyzes the conversion of 1 µmole hydrogen peroxide per minute at the following analytical conditions: 2.0 mM hydrogen peroxide, 0.46 mM 2,2'-azino-bis(3-ethylbenzothiazoline-6-sulfonate), 0.086M phosphate buffer, pH 7.0, incubated at 40° C., photometrically followed at 418 nm. 1 KPOXU = 1000 POXU.

We claim:

1. A method for obtaining a crystallized microbial protein from an aqueous mixture of proteins, said method comprising of the steps of:

(a) obtaining a microbial culture broth having a mixture of proteins, comprising a desired protein selected from the group consisting of an oxidoreductase, a protease, a lipase, a cellulase and an amylase;

(b) adjusting the salt concentration of said protein mixture at or below 1.5 Molar;

(c) adding a water soluble polymer to the protein mixture of step (b);

(d) stirring the polymer-containing protein mixture of step (c) for up to 48 hrs; and (e) recovering the desired protein in crystalline form from the stirred mixture of step (d).

2. A method according to claim 1, which method further comprises concentration of the protein mixture prior to adding the water soluble polymer.

3. The method according to claim 2, wherein the protein mixture is concentrated by ultrafiltration, diafiltration, dialysation, evaporation or precipitation.

4. A method according to claim 2, in which the protein mixture is concentrated to a protein content of from 0.1 to 25% w/w.

5. A method according to claim 1, in which the water soluble polymer is a glycol or a mixture of glycols.

6. A method according to claim 5, in which the glycol is polyethylene glycol or polypropylene glycol.

7. A method according to claim 6, in which the polyethylene glycol has a MW of from 200 to 10000.

8. A method according to claim 5, in which the glycol is added in concentrations of 1–50% w/w.

9. A method according to claim 1, in which a salt is added to the mixture of proteins in a concentration of up to 1.5 Molar.

10. A method according to claim 9, in which the added salt is a salt of Magnesium, Calcium, Sodium, Potassium or Ammonium.

11. A method according to claim 10, in which the anion of the salt is selected from the group consisting of Chloride, Formiate, Acetate and Sulphate.

12. A method according to claim 1, in which the pH of the solution is adjusted to the optimum of the crystallization.

13. A method according to claim 12, in which pH is adjusted to pI±1.

14. A method according to claim 9, wherein a salt is added to the mixture of proteins in a concentration of up to 1.5 Molar, and wherein the pH of the solution is adjusted to the optimum of the crystallization.

15. The method of claim 4, wherein the protein mixture is concentrated to a protein content of from 0.5 to 15% w/w.

16. The method of claim 15, wherein the protein mixture is concentrated to a protein content of from 1 to 10% w/w.

17. A method according to claim 8, in which the glycol is added in concentrations of 2–40% w/w.

18. A method according to claim 9, in which a salt is added in a concentration of up to 1.0M.

19. A method according to claim 14, in which a salt is added to a concentration of up to 1.0M.

* * * * *